(12) United States Patent
Jayaprakash et al.

(10) Patent No.: US 9,868,946 B2
(45) Date of Patent: Jan. 16, 2018

(54) METHOD OF ISOLATING PURE MITOCHONDRIAL DNA

(71) Applicant: GIRIHLET INC., Brooklyn, NY (US)

(72) Inventors: Anitha Jayaprakash, New York, NY (US); Ravi Sachidanandam, Brooklyn, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/440,694

(22) PCT Filed: Nov. 1, 2013

(86) PCT No.: PCT/US2013/068042
§ 371 (c)(1),
(2) Date: May 5, 2015

(87) PCT Pub. No.: WO2014/071178
PCT Pub. Date: May 8, 2014

(65) Prior Publication Data
US 2015/0275200 A1    Oct. 1, 2015

Related U.S. Application Data

(60) Provisional application No. 61/768,142, filed on Feb. 22, 2013, provisional application No. 61/722,664, filed on Nov. 5, 2012.

(51) Int. Cl.
| | |
|---|---|
| *C12N 9/16* | (2006.01) |
| *C12N 9/14* | (2006.01) |
| *C12N 9/22* | (2006.01) |
| *C12N 1/08* | (2006.01) |
| *C12N 15/10* | (2006.01) |

(52) U.S. Cl.
CPC ........... *C12N 15/1006* (2013.01); *C12N 9/16* (2013.01); *C12N 15/1003* (2013.01); *C12Y 301/11005* (2013.01)

(58) Field of Classification Search
CPC .. C12N 15/1003; C12N 15/1006; C12N 9/16; C12Y 301/11005
USPC ................... 435/196, 199, 195, 270
See application file for complete search history.

(56) References Cited

U.S. PATENT DOCUMENTS 8,008,008 B2 *   8/2011   Parr ................. C12Q 1/6886
                                                           435/6.12
2005/0069991 A1 *   3/2005   Hyman ................ C12N 9/1205
                                                           435/91.2

FOREIGN PATENT DOCUMENTS

| EP | 0324647 | 8/1994 |
| WO | 9213963 A1 | 8/1992 |
| WO | 03070945 A1 | 8/2003 |
| WO | 2010048605 A1 | 4/2010 |
| WO | 2014071178 A1 | 5/2014 |

OTHER PUBLICATIONS

Wilcox et al., Mechanism of DNA degradation by the ATP-dependent DNase from Hemophilus influenzae Rd. The J. biol. Chem., 1976, vol. 251 (19): 6127-6134.*
Agencourt AMPure XP: Instruction Manual, 2013 version B37419AA, Total 36 pages.*
Epicentre Master Pure Complete DNA and RNA purification kit, Lit.# 110, Sep. 2010, Total 16 pages.*
Friedman et al., An adenosine triphosphate-dependent deoxyribonuclease from Hemophilus influenzae Rd. The J. Biol. Chem., 1972, vol. 247 (9): 2859-2865.*
Hawkins et al., DNA purification and isolation using a solid-phase. Nuc. Acids Res., 1994, vol. 22 (21): 4543-4544.*
Exonuclease V (RecBCD) Catalog #M0345S; 4 pages down loaded from New England Biolabs site on Sep. 13, 2016.*
Plasmid-SafeTM (EPICENTRE; commercial Hind Exonuclease V; 2 pages down loaded from http://www.epibio.com/ on Sep. 13, 2016.*
Epicentre an Illumina Company: RecBCD Nuclease; 2 pages down loaded from http://www.epibio.com/ on Mar. 23, 2017.*
Smith GR., RecBCD enzyme. Nuc. Acids Res., and Mol. Biol., 1990, vol. 4: 78-98.*
Balagurumoorthy, P., et al., Method to Eliminate Linear DNA from Mixture Containing Nicked Circular, Supercoiled, and Liner Plasmid DNA, Analytical Biochemistry, vol. 381, pp. 172-174 (2008).
Clayton, D., et al., Isolation of Mitochondria from Tissue Culture Cells, Cold Spring Harb. Protoc. 2014, pdb. prot080002, 4 pgs. (2014).
Dillingham, M., et al., RecBCD Enzyme and the Repair of Double-Stranded DNA Breaks, Microbiology and Molecular Biology Reviews, vol. 72, No. 4, pp. 642-671 (2008).
Hornig-Do, H., et al., Isolation of Functional Pure Mitochondria by Superparamagnetic Microbeads, Analytical Biochemistry, vol. 389, pp. 1-5 (2009).
Jayaprakash, A., et al., Stable Heteroplasmy at the Single-Cell Level is Facilitated by Intercellular Exchange of mtDNA, Nucleic Acids Research, vol. 43, No. 4, pp. 2177-2187 (2015).

(Continued)

*Primary Examiner* — Ganapathirama Raghu
(74) *Attorney, Agent, or Firm* — Benesch, Friedlander, Coplan & Aronoff LLP (57) ABSTRACT

A method for preparing circular double stranded mitochondrial DNA (mtDNA) substantially free of genomic DNA (gDNA) comprising the steps of: providing a cellular lysate free of protein and RNA contaminants, precipitating cellular debris and proteins out of said lysate and obtaining a solution comprising purified circular double stranded mitochondrial DNA (mtDNA) and genomic DNA (gDNA), incubating said solution with an amount of Hind Exonuclease V for a time and at a temperature effective to cleave non-circular DNA and obtain circular double stranded mtDNA, incubating said circular double stranded mtDNA with an amount of Ampure beads effective to bind said circular double stranded mtDNA, washing said beads with ethanol, and eluting said mtDNA from said beads, wherein said method is free of ultra-centrifugation.

9 Claims, 5 Drawing Sheets

(56) References Cited

OTHER PUBLICATIONS

Miranda, A., et al., Chromosomal Lesion Suppression and Removal in *Escherichia coli* via Linear DNA Degradation, Genetics, vol. 163, pp. 1255-1271 (2003).
Sims, N., et al., Isolation of Mitochondria from Rat Brain Using Percoll Density Gradient Centrifuguation, Nature Protocols, vol. 3, No. 7, pp. 1228-1239 (2008).
Zhou, J., et al., Method to Purify Mitochondrial DNA Directly from Yeast Total DNA, Plasmid, vol. 64, pp. 196-199 (2010).
International Application PCT/US2013/068042, International Search Reported dated Jan. 29, 2014, 2 pgs.
PCT/US2013/068042 PCT Notification of Transmittal of the International Search Report and the Written Opinion of the International Searching Authority.
Kent W. Wilcox, et al., Mechanism of DNA Degradation by the ATP-dependent DNase from Hemophilus influenzae Rd, The Journal of Biological Chemistry, vol. 251, No. 19, Issue of Oct. 10, pp. 6127-6134, 1976.
Yoshihiro Higuchi, et al., Purification of All Forms of HeLa Cell Mitochondrial DNA and Assessment of Damage to It Caused by Hydrogen Peroxide Treatment of Mitochondria or Cells, The Journal of Biological Chemistry, vol. 270, No. 14, Issue of Apr. 17, pp. 7950-7956, 1995.

\* cited by examiner

METHOD OF ISOLATING PURE MITOCHONDRIAL DNA

CROSS-REFERENCE TO RELATED APPLICATIONS

This application claims priority under 35 U.S.C. §119(e) from Provisional Application Ser. Nos. 61/722,664 filed Nov. 5, 2012 and 61/768,142 filed Feb. 22, 2013. The entire disclosures of said applications are hereby incorporated by reference in their entirety.

TECHNICAL FIELD

This invention pertains to methods to isolate and purify mitochondrial DNA substantially free of genomic DNA and kits for use in the method.

BACKGROUND OF THE INVENTION

Mitochondrion is a critical organelle present in most of the eukaryotic cells. Commonly known as the "power house of the cell" it is not only responsible for the production of ATP, but also generates superoxide ions and regulates cellular calcium levels and apoptotic cell death stimuli. Overall, it is involved in multiple cellular processes including Oxidative Phosphorylation, Apoptosis, Organizing Cell Signaling Pathways, and Regulation of Cell Cycle. Human Mitochondrial DNA (mtDNA) consists of 16,569 bp in a double-stranded circular structure and encodes 37 genes (13 respiratory genes, 2 rRNAs and 22 tRNAs).

Figure 1:
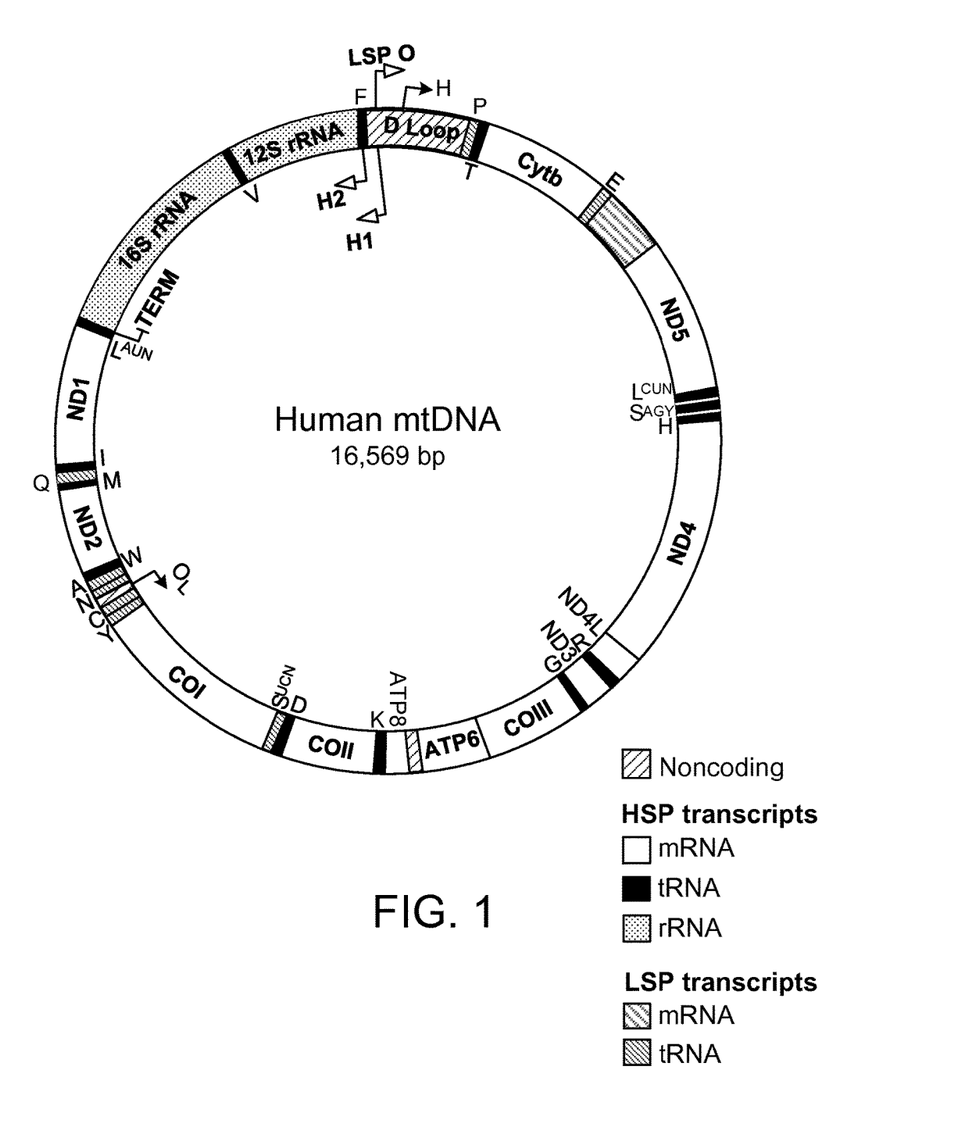
FIG. 1 is a genetic map of the human mitochondrion (taken from Falkenberg, M. Annu. Rev. Biochem. 76:679-699' 2007).

FIG. 1 is a map of human mitochondrial DNA. Genes are transcribed as polycistronic RNA precursors that are later processed by RNAse P which recognizes the secondary structure of the tRNAs flanking each gene. The D-loop is non-coding and acts as a regulatory region, containing the H-chain and L-chain transcription initiation sites. Origins of replication are also shown.

mtDNA is used to study human migration and evolution. mtDNA is inherited from the mother, and does not undergo recombination, thereby providing a molecular clock to study evolutionary changes. Mutations in mtDNA are implicated in various diseases including metabolic disorders, neurodegenerative diseases, and cancer. More than 200 different mutations in the mtDNA have been associated with human diseases. Thus, sequencing the mitochondria can provide clues to origins of diseases as well as help delineate changes due to aging as well as somatic and germ-line mutations that might cause disorders. With the advent of next generation sequencing technology, it is now easy to deeply sequence DNA. In order to sequence the mtDNA, it is important to isolate the mtDNA effectively without any nuclear DNA contamination, because there are significant regions of homology between the nuclear and mitochondrial DNA, making it difficult to unambiguously identify the origin of short read fragments. Owing to the immense size difference between human nuclear DNA (6 billion bp) and human mtDNA (16 kb), small amounts of nuclear DNA contamination can lead to most of the DNA sequences being of nuclear origin. All current methods of isolating mitochondrial DNA involve first isolating the organelle and then purifying its DNA using standard protocols. These methods involving CsCl gradients, take advantage of the differential density of the circular mtDNA and the nuclear genomic DNA. The organelle separation leads to the loss of material, both due to the high forces involved (which can disrupt organelles and genomic DNA) and co-separation of the organelles with nuclear DNA due to similar densities. What is needed in the art are methods to efficiently and rapidly isolate mtDNA, while avoiding contamination with nuclear DNA.

SUMMARY OF THE INVENTION

Disclosed herein is a method that enables the isolation of mtDNA of high purity, i.e. free of nuclear DNA contamination. In this technique, cells are lysed and total genomic DNA (gDNA) is isolated and incubated with an exonuclease, which cleaves DNA that is not double stranded, circular and therefore, digests the nuclear DNA and spares the circular, double stranded mtDNA. This method avoids the use of high-speed ultra-centrifugation for organelle isolation. The organelle isolation method does not yield high-purity (>80%) mtDNA and requires disruptive techniques. The method of the present invention, in contrast, gives consistently high purity yields (>90% purity). The repeat content in the sequenced reads can be used to estimate the level of contamination by genomic DNA.

This invention makes feasible deep sequencing of mtDNA without the need for any additional modifications, making it ideal for clinical and analytical applications.

In one aspect, the present invention provides a method for preparing circular double stranded mitochondrial DNA (mtDNA) substantially free of genomic DNA (gDNA) comprising the following steps, i) lysing cells to form a lysate, ii) incubating said lysate with an amount of Proteinase K effective to digest proteins in said lysate, iii) digesting any RNA in said lysate, iv) adding a protein-precipitation reagent to said lysate to obtain precipitate and a supernatant, v) precipitating total DNA in said supernatant and forming a pellet, vi) suspending the supernatant pellet in a buffer, vii) incubating the suspended pellet at about 70° C. for about 30 minutes to form a solution, viii) incubating the solution with an amount of an exonuclease for a time effective to cleave non-circular double stranded DNA and obtain circular double stranded mtDNA, ix) incubating said circular, double stranded mtDNA with an amount of AMPure® beads effective to bind said circular double stranded mtDNA, x) washing said beads with ethanol and xi) eluting said mtDNA from said beads; wherein said method is free of ultra-centrifugation.

In another aspect, the present invention provides a method for preparing circular, double stranded mitochondrial DNA (mtDNA) substantially free of genomic DNA (gDNA) comprising the steps of providing a solution comprising mitochondrial DNA (mtDNA) and genomic DNA (gDNA) purified from a cell, incubating the solution with an amount of an exonuclease selected from the group consisting of Hind Exonuclease V, T5 Exonuclease and Exonuclease V, for a time and at a temperature effective to cleave non-circular DNA and obtaining circular double stranded mtDNA, incubating said circular double stranded mtDNA with an amount of AMPure® beads effective to bind said circular double stranded mtDNA, washing said beads and eluting said mtDNA from said beads, wherein said method is free of ultra-centrifugation.

In yet another aspect, the present invention provides a kit for isolating mitochondrial DNA (mtDNA) substantially free of genomic DNA (gDNA) comprising in separate containers an exonuclease selected from the group consisting of Hind Exonuclease V, exonuclease V and T5 Exonuclease V, AMPure® beads, mitochondrial DNA primers and instructions for use.

In a further aspect, the present invention provides a method for preparing circular, double stranded mitochondrial DNA (mtDNA) substantially free of genomic DNA (gDNA) comprising the steps of providing a cellular lysate free of protein and RNA contaminants, precipitating cellular debris and proteins out of said lysate and obtaining a solution comprising purified circular, double stranded mitochondrial DNA (mtDNA) and genomic DNA (gDNA), incubating said solution with an amount of Hind Exonuclease V for a time and at a temperature effective to cleave non-circular DNA and obtain circular double-stranded mtDNA, incubating said circular double stranded mtDNA with an amount of AMPure® beads effective to bind said circular double stranded mtDNA, washing said beads with ethanol, and eluting said circular double stranded mtDNA from said beads, wherein said method is free of ultra-centrifugation.

In a still further aspect, the present invention provides a method for preparing circular double stranded DNA substantially free of linear DNA comprising the steps of providing a sample comprising purified circular double stranded DNA and linear DNA free of protein and RNA contaminants; incubating said sample with an amount of Hind Exonuclease V for a time and at a temperature effective to cleave non-circular DNA and obtain circular double stranded DNA; incubating said circular DNA with an amount of AMPure® beads effective to bind said circular double stranded DNA; washing said beads with ethanol, and eluting said circular double stranded DNA from said beads, wherein said method is free of ultra-centrifugation.

These and other aspects of the present invention will be apparent to those of ordinary skill in the light of the present description, accompanying claims and appended drawings.

DETAILED DESCRIPTION OF THE INVENTION

The term "about" or "approximately" is defined herein to mean within an acceptable error range for the type of value and method of measurement. For example, it can mean within 20%, more preferably within 10%, and most preferably still within 5% of a given value or range. Alternatively, especially in biological systems, the term "about" means within about one log (i.e., an order of magnitude), preferably within a factor of two of a given value.

"Free of centrifugation" is defined herein as the absence of ultracentrifugation at high speeds (over 20,000 rpm) in certain media (i.e. sucrose or cesium chloride) used in organelle isolation.

The present invention provides methods to prepare mitochondrial DNA (mtDNA) which is substantially free of genomic DNA contamination. Total DNA from a cell consists of less than 1% of mt DNA. In one preferred non-limiting embodiment, "substantially free of genomic DNA" is defined as comprising greater than 80% mtDNA.

Pursuant to the present invention, total DNA is extracted from cells and tissues using techniques, which maintain the mtDNA in circular form. In a non-limiting embodiment, the Epicentre® protocol for total DNA extraction which employs the MasterPure™ DNA purification kit ((MasterPure™, Epicentre® MCD85201, Epicentre Biotechnologies®, Madison, Wis.) is used. The kit provides all of the materials needed for DNA isolation including reagents, buffers and enzymes. Alternately, one of ordinary skill in the art could assemble the components of the kit such as the lysis buffer, protein precipitation solution and specific enzymes such as T5 Exonuclease V, exonuclease V or Hind Exonuclease V, proteinase-K and RNaseA from any alternative vendor, and carry out the DNA purification using the method described herein.

A detailed protocol is shown below in Example 1. The procedure uses a proteinase-K treatment step as soon as the cells are disrupted, which kills all enzymes (proteins), thereby protecting the DNA from being damaged by endonucleases and yields purified total DNA (gDNA plus mtDNA).

The method of the present invention has several features that have never been used previously to obtain mtDNA (or any DNA). The method uses an exonuclease to eliminate nuclear DNA and preserve mtDNA. It avoids the use of ultracentrifugation to isolate the organelle to obtain purified DNA and uses AMPure® XP beads to purify the mtDNA without filtration or centrifugation (Agencourt® AMPure® XP-PCR Purification, Beckman Coulter®, Inc, Brea, Calif.).

Mitochondrial DNA can be purified with high efficiency by using any exonuclease which digests single-stranded linear DNA double-stranded linear DNA and single-stranded circular DNA and spares circular and supercoiled double stranded DNA. Non-limiting examples of exonucleases for use in the invention include, an ATP-Dependent DNase, Hind Exonuclease V (commercially available as PlasmidSafe™ from Epicentre Biotechnologies®, Madison, Wis.) or a T5 Exonuclease or an Exonuclease V, also known as RecBCD Nuclease (New England Biolabs®, Ipswich, Mass.). The enzymes can be used alone or in any combination.

In order to obtain mtDNA, total DNA from cells or tissues was extracted using the Epicentre® MasterPure™ DNA purification kit. Briefly, cells were collected and lysed in a solution containing 1 µL of Proteinase K into 300 mL of Tissue and Cell Lysis Solution for each sample. The mixture was further incubated with RNase A to digest the RNA present therein. All the debris and proteins were precipitated out of the solution using the Protein Precipitation Reagent provided in the kit. The supernatant that contained the total DNA was then precipitated using isopropanol and the pellet was re-suspended in 35 µL of TE Buffer. The details are set forth in Example 1 below.

To inactivate any remaining proteinase K left over from the total DNA extraction, the solution was incubated at 70° C. for 30 minutes. The concentration of DNA was measured using nanodrop (www.nanodrop.com).

mtDNA Extraction

To isolate mtDNA, a commercially available ATP-dependent exonuclease (PlasmidSafe™ from Epicentre® (Madison, Wis., Catalogue number E3101K) that cleaves non-circular DNA was used. Briefly, 4 µg of genomic DNA was incubated with 10 units of this enzyme for 12 hours at 37° C. in a 50 µL reaction. After incubation, the circular DNA was purified using AMPure® XP beads. The details are set forth in Example 2 below.

dNTP and Enzyme Clean-up (AMPure® Beads)

AMPure® beads (90 µL) were added to the sample (50 µL) and mixed thoroughly by pipetting. The solution was incubated at RT for 10 min, and then placed onto a magnetic rack for 5 min until the solution cleared and beads condensed on the side of tube. The supernatant was removed and the beads were washed twice with 80% ethanol. Excess ethanol was removed; water was added to the beads and incubated at RT for 10 min. The sample was placed on a magnetic rack and the supernatant that contained the mtDNA was transferred to a new tube. A detailed protocol is shown in Example 3 below.

To test the activity of PlasmidSafe™ in its ability to spare circular DNA structures, total gDNA was isolated from the 293T cell line (human kidney fibroblast cells) and was incubated with PlasmidSafe™ as per the protocol above. The presence of gDNA and mtDNA was then tested for using specific primers by PCR. As a control, total gDNA was also amplified before digestion. Six different genes each were tested for gDNA and mtDNA. Amplified products were then electrophoresed on a 2% Agarose gel. The results are shown in FIG. 2.

Figure 2:
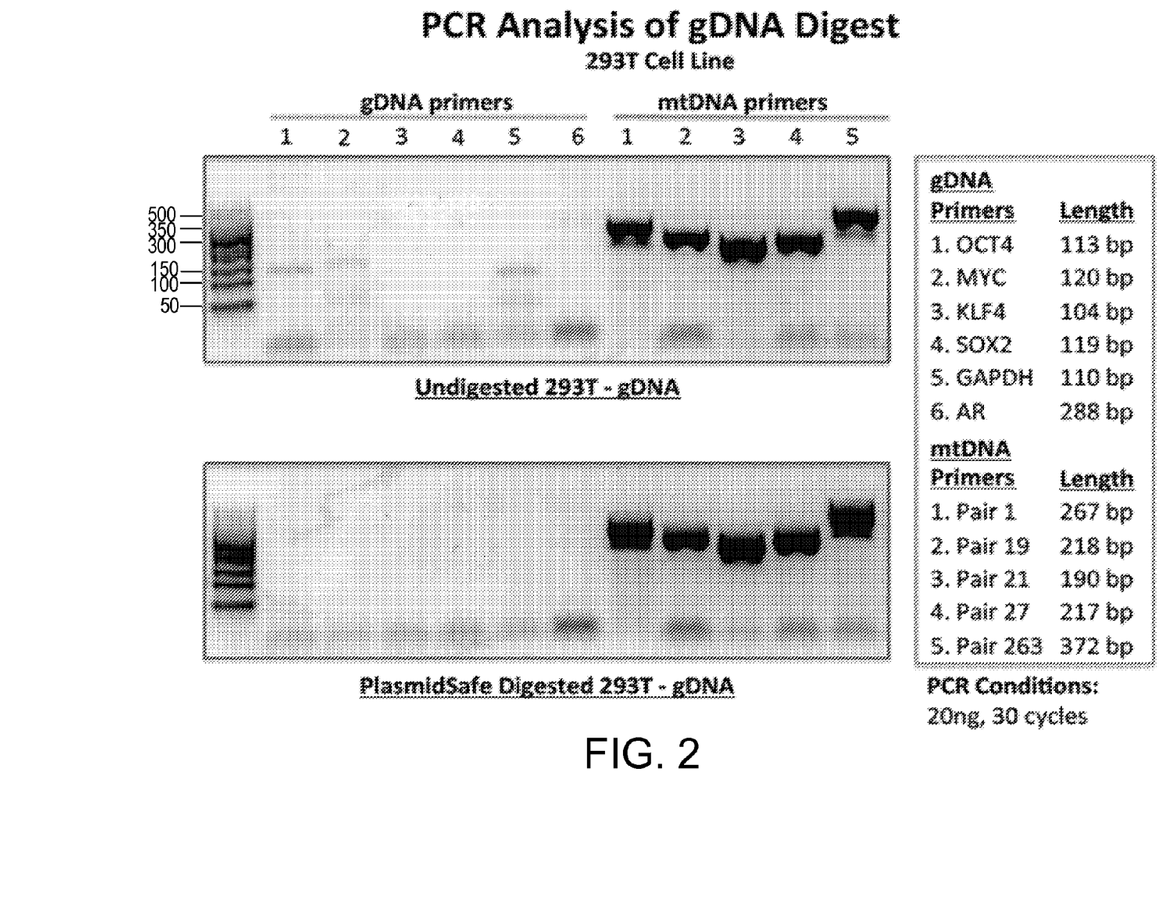
FIG. 2 is photographs of gels showing PCR analyses of total DNA digests from 293T cells using gDNA and mtDNA primers and (top panel) undigested 293T gDNA or (lower panel) PlasmidSafe™ digested 293T gDNA.

In FIG. 2, PCR primers for 6 different genomic DNA genes (OCT4, MUC, KLF4, SOX2, GAPDH and AR) and 5 primers specific to 5 different regions of the mitochondria (pair 1, 19, 21, 27 and 263) were designed. All the PCR products were run on a 2% Agarose gel. The top panel shows the amplification of all the regions before PlasmidSafe™ digestion. The size of each of the expected PCR product is displayed on the right side. Before digestion, clear bands for all the regions (g.DNA+mtDNA) are seen, but after digestion (lower panel), bands only specific to mtDNA appear indicating that the PlasmidSafe™ is efficiently sparing circular DNA structures like the mitochondria.

It was clear that the digestion worked and all gDNA had been cleaved leaving the mtDNA intact.

Figure 3:
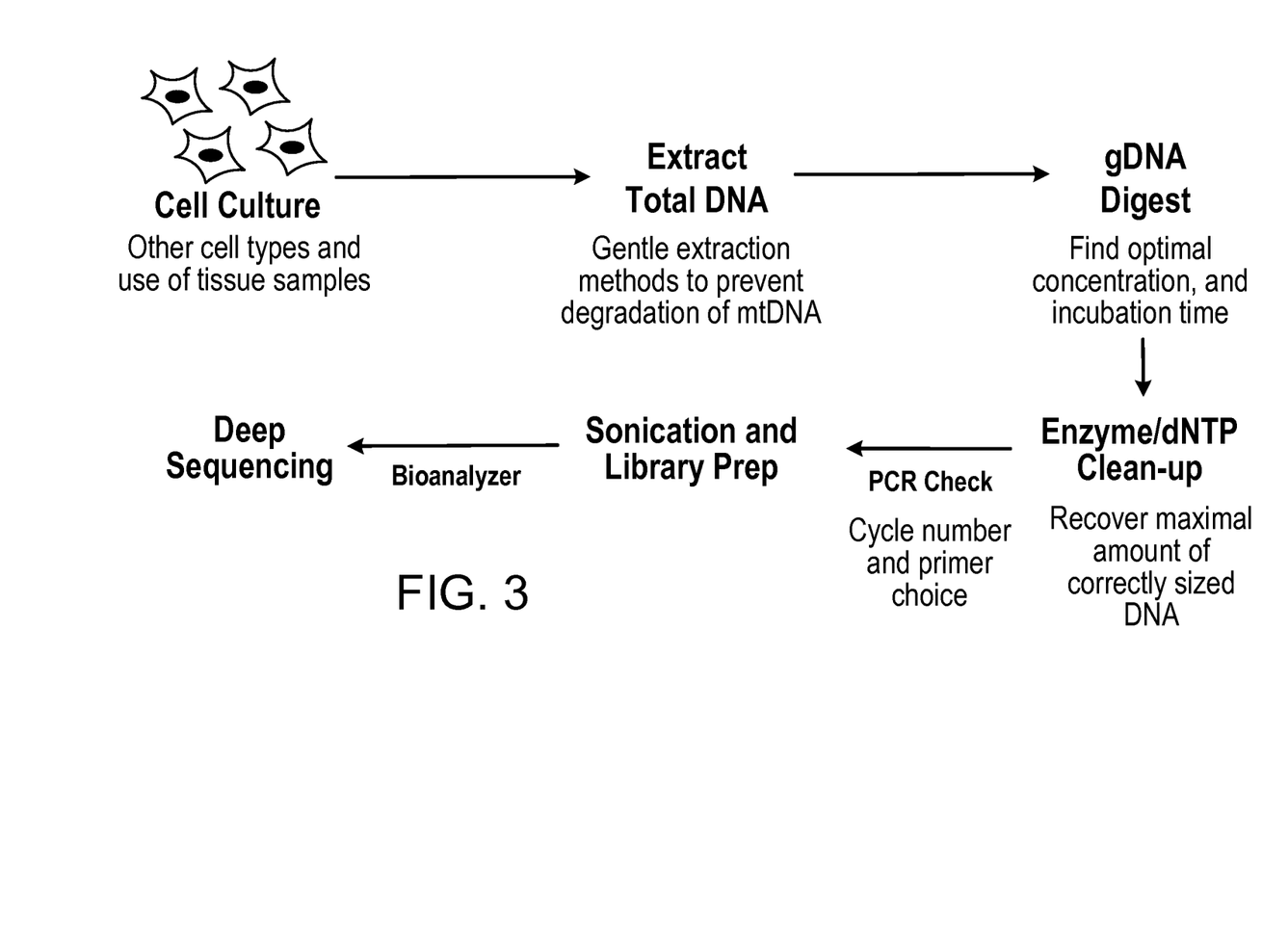
FIG. 3 is a brief outline of the steps involved in the method of the present invention beginning with cells in culture to production of a library for deep sequencing.

Since only 6 genes were tested, these samples were taken to deep sequencing, to check for purity as well as coverage of the mtDNA from these PlasmidSafe™ digests. The protocol provided by Illumina, Inc. (San Diego, Calif.) was followed to prepare these libraries. Briefly, digested samples were purified using AMPure® beads (Hawkins, T. L., et al. (1994). DNA purification and isolation using a solid-phase. Nucl Acid Res 22(21):4543-4; Lis, J. Methods Enzymol. 65, 347-353, 1980; www.beckmancoulter.comi-wsrportal/wseresearch-and-discovery/products-and-services/nucleic-acid-sample-preparation/agencourt-Ampure-xp-per-purification/index.htm), then fragmented to about 100 bp inserts using Covaris® (covarisinc.com/). The ends of all of the double stranded inserts were blunted, and then an A base was added to their 3' ends. Known sequences were ligated to all the inserts and this library was amplified with primers against the known sequences by PCR (FIG. 3). The quality and quantity of the library was checked using a bioanalyzer before hybridizing to the Illumina® flow-cell for deep sequencing.

Figure 4:
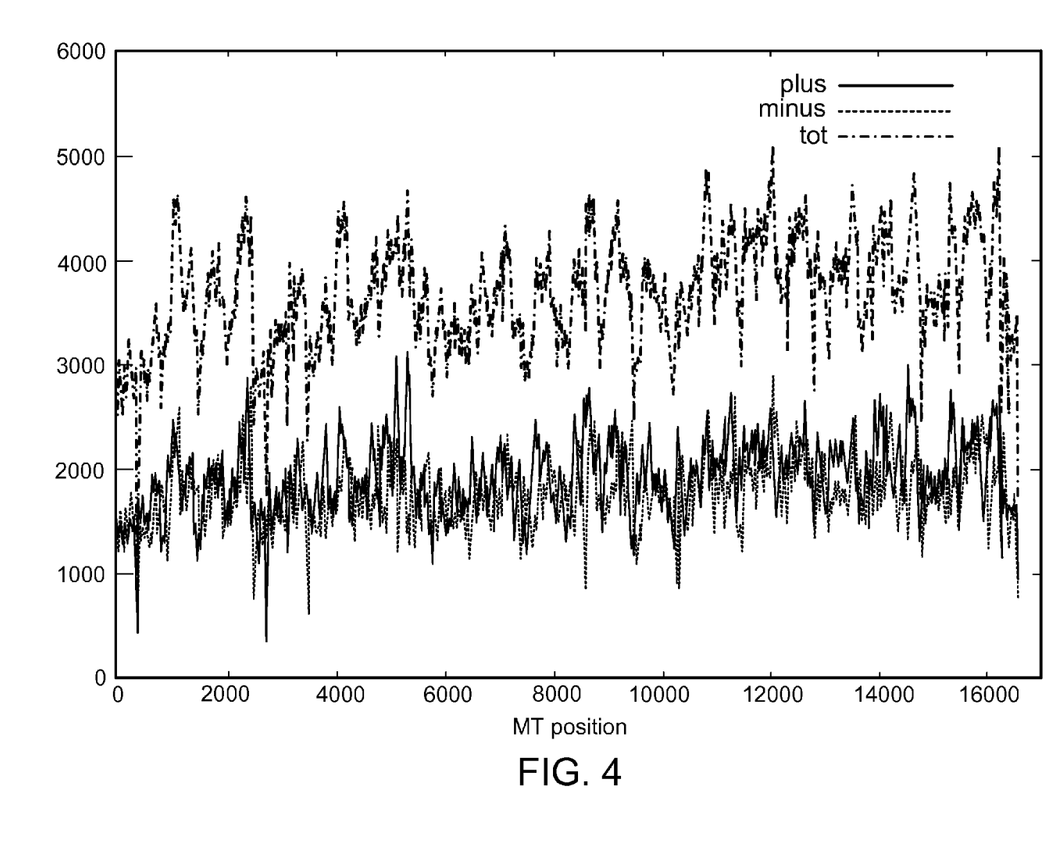
FIG. 4 is a graph showing the mapping of sequence reads to each of the strands separately, the plus strand, the minus strand and the sum of both strands.

The sample library was run on an Illumina® MiSeq machine and a 50 bp Single read sequencing was performed (www.illumina.com/systems/miseq.ilmn). A total of 3.05 million reads were obtained of which 1.233 million mapped to human mtDNA and 50,000 mapped to genomic DNA. The remaining 1.85 million was adapter dimers and other sequencing artefacts. Including only mappable reads, genomic contamination was 1.2% (or 98.8% of the reads were mtDNA) with a minimum of 1000× coverage across the mtDNA genome (FIG. 4). This is sufficient depth to easily assemble the reads and call SNPs and variants on this data. Bisulfite sequencing is also easily done to test for methylation changes.

Figure 5:
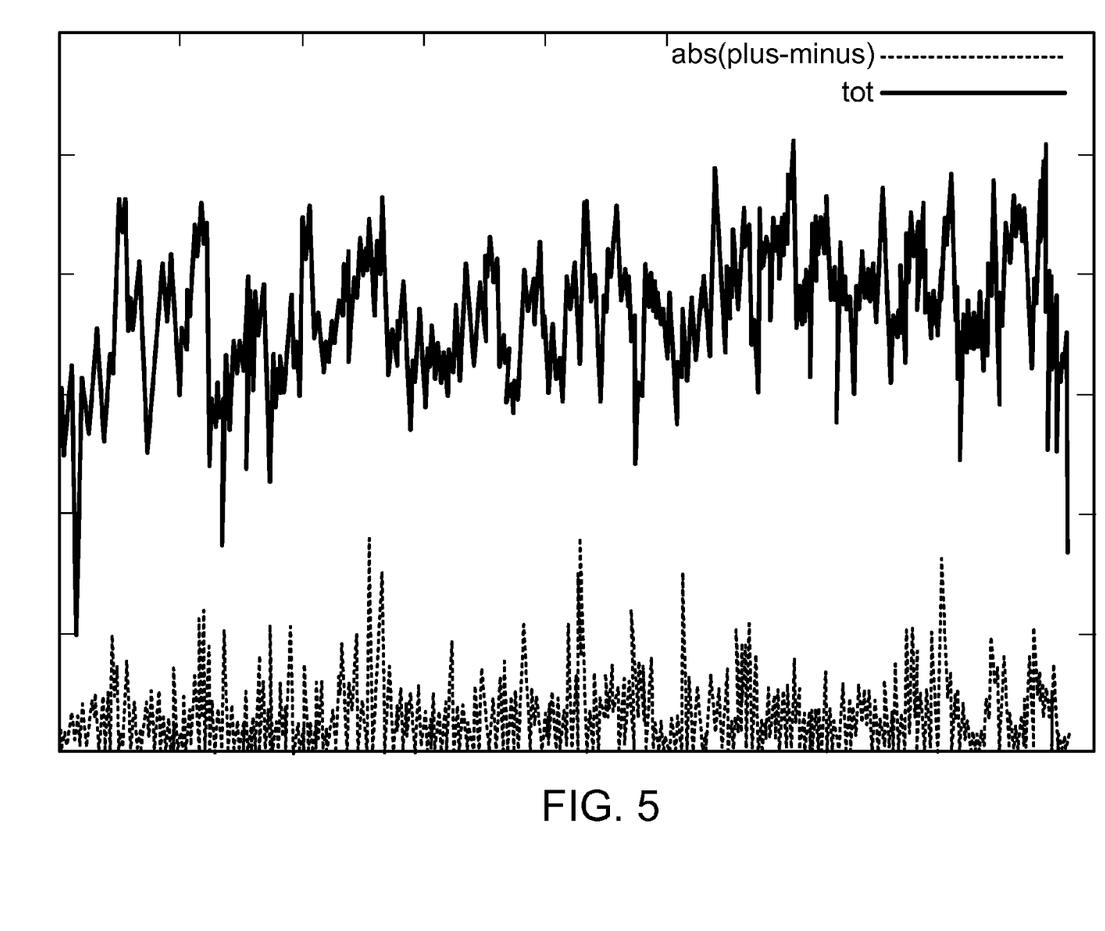
FIG. 5 is a graph showing the total coverage and the absolute difference in coverage between the reads on the positive and negative strands.

FIG. 5 shows the total coverage and absolute difference in coverage between the reads on the positive and negative strands. The difference is small compared to the total coverage, suggesting uniform ad unbiased sampling over the whole mtDNA sequence.

With the dramatic increase in throughput made possible by next-generation DNA sequencing technologies, sodium bisulfite conversion followed by massively parallel sequencing (Bisulfite-seq) has become an increasingly popular method for investigating epigenetic profiles in the human genome (reviewed in Laird P W, Nat Rev Genet. 2010 March; 11(3):191-203.

Principles and Challenges of Genomewide DNA Methylation Analysis).

Presented herewith is a novel and a quick way to isolate mtDNA of high purity and quality. It has also demonstrated the ability to perform next generation sequencing experiments on the isolated mtDNA. This allows for the mtDNA to be applied in a clinical as well as research setting.

Built-into the method of the present invention is a way to estimate the nuclear genomic contamination, and hence the reliability of the data. Repeats that are sequenced arise from the nuclear genome. There are no repeats in the mitochondrial genome. Thus, by mapping reads to repeats, one can estimate the fraction of the reads that come from the nuclear genomic DNA. From the 20 samples that have been sequenced to date using the method claimed herein, the worst sample contained 3.0% of repeat content; most were less than 2%, some below 1%, This shows that the claimed method yields over 95% mitochondrial DNA after the treatment. This improves the reliability of single nucleotide polymorphisms (SNPs) called, since almost each of the mitochondrial DNA has a nuclear homologue, which can affect the accuracy of the SNP calls.

In addition, the methods disclosed herein can be used to isolate and purify circular DNA from any source, such as from chloroplasts (in plants) and mitochondria, in most eukaryotes, (answers.yahoo.com/question/index?qid=20100822165324AAM53Cq, as well as from bacterial DNA (www.sci.sdsu.edu/~smaloy/MicrobialGenetics/topics/chroms-genes-prots/chromosomes.html) which can be isolated from infected tissues or cultures.

The Examples below describe the materials and detailed methods for preparing a mtDNA library.

The present invention is described further below in working examples, which are intended to describe the invention without limiting the scope thereof.

Example 1

Total DNA Extraction

Total DNA Purification (MasterPure™, Epicentre® MCD85201)

1. Pellet cells (0.5-1.0×10$^6$ mammalian cells), then remove supernatant leaving about 25 µL, enough to cover pellet.

2. Re-suspend pellet by vortexing until homogenous.

3. Dilute 1 μL of Proteinase K into 300 mL of Tissue and Cell Lysis Solution for each sample, then add to sample and mix thoroughly by inverting and briefly vortexing.

4. Incubate on 65° C. heat block for 15 min, mixing by inversion every 5 min.

5. Cool samples at RT for 3 min and add 1 μL of 5 mg/mL RNase A to the sample; mix thoroughly by inverting.

6. Incubate at 37° C. for 30 min.

7. Place samples one ice for 5 min.

8. Add 150 μL of MPC Protein precipitation Reagent to each 300 μL of sample and mix thoroughly by inverting 9. Pellet precipitated debris by centrifugation at 4° C. for 10 min at 12000 g.

10. Remove viscous aggregate of precipitated debris using pipet to slide out into waste.

11. Centrifuge samples again at 4° for 5 min at 12000 g and transfer supernatant to new tube.

12. Add 500 μL of isopropanol to recovered supernatant and invert tube 40 times.

13. Pellet DNA by centrifugation at 4° C. for 10 min.

14. Pour off isopropanol and wash twice with 1 mL of 70% ethanol.

15. Resuspend DNA in 35 μL of TE Buffer.

16. Incubate at 70° C. for 30 minutes.

17. Measure sample concentration with nanodrop.

1. Pipet volume of extracted total DNA equal to 4 μg into a clean tube

2. Use conditions as follows to produce a 50 μL reaction:
   a. PlasmidSafe™ Buffer 10×: 5 μL
   b. ATP (25 mM): 2 uL
   c. PlasmidSafe™ Enzyme (10 units/μL): 1 μL
   d. Total DNA (4 μg): X μL
   e. $H_2O$: up to 50 μL 3. Incubate at 37° C. for 12 hours Example 3 dNTP and Enzyme Clean-Up (AMPure® Beads)

1. Add 90 μL of AMPure® beads to 50 μL of sample and mix thoroughly by pipetting.

2. Incubate at RT for 10 min, and then place onto magnetic rack for 5 min until solution clears and beads condense on side of tube.

3. Remove supernatant without disturbing beads and discard.

4. Add 80% ethanol to sample and allow beads to settle for 3 min, remove ethanol. Repeat once.

5. Allow excess ethanol to dry for one min without over drying beads.

6. Add 30 μL of $H_2O$, making sure to mix well with beads by pipetting.

7. Incubate at RT for 10 min and then place onto magnetic rack for 3 min.

8. Transfer supernatant to a clean tube.

Example 4

PCR Check (NEB Cat. M0484S)

1. Use conditions as follows for a 20 μL reaction using mitochondria and genomic primers:
   a. 2×HS Master Mix: 10 μL
   b. Forward Primer (5 μM): 0.8 μL
   c. Reverse Primer (5 μM): 0.8 μL
   d. $H_2O$: 7.4 μL
   e. PS Digested DNA: 1 μL 2. Use following conditions for thermocycler:
   a. 94° C. for 30 sec
   b. 94° C. for 15 sec
   c. 60° C. for 30 sec
   d. 68° C. for 45 sec
   e. Cycle through steps b-d 29 more times
   f. 68° C. for 5 min, 4° C. indefinite 3. Run samples on 2% agarose gel and check for presence of mtDNA and absence of gDNA in order to proceed with subsequent steps.

Example 5

Fragmentation (Covaris®)

1. Bring volume of AMPure® purified sample up to 120 μL with pure $H_2O$

2. Transfer sample to Covaris® tube and set up sonication for fragments of sizes 150-250 bp as follows:
   a. Duty Cycle: 10%
   b. Intensity: 5
   c. Cycles/Burst: 50
   d. Time: 1,200 seconds 3. After sonication, spin down sample in speedvac for two hours at 45° C. to bring down volume below 50 μL.

Example 6

Library Preparation (TrueSeq)

Perform End Repair

1. Add 40 μL of End Repair Mix to the sample. Mix well by pipetting.

2. Incubate:
   a. 30° C. 30 min

AMPure® Clean up after End Repair

1. Vortex the AMPure® XP beads until they are homogenous. Add 160 μL of the AMPure® XP beads to the sample tube and mix by pipetting.

2. Incubate at RT for 15 min.

3. Place the tube at magnetic stand for 5 min

4. Discard supernatant.

5. Wash the beads with 200 μL of 80% EtOH without disturbing the beads.

6. Wait 30 sec. Discard the supernatant.

7. Repeat the wash with 80% EtOH

8. Air dry the beads for 15 min at RT

9. Resuspend the beads in 7.83 μL of Resuspension Buffer. Mix by pipetting.

10. Incubate the sample at RT for 2 min

11. Place sample in Magnetic stand for 5 min.

12. Transfer the supernatant (ds cDNA, 5.83 μL) to a new tube

A Tail Addition to 3' Ends

1. Add 4.17 μL of A-Tail Mix to the sample. Mix by pipetting.

2. Incubate:
   a. 37° C.-30 min

NO CLEAN UP AFTER A-TAIL=PROCEED to Ligation IMMEDIATELY!!

Ligate RNA Adapters

1. Add the following:
   a. 0.83 μL of DNA Ligase Mix
   b. 0.83 μL of RESUSPENSION BUFFER
   c. 0.83 μL of RNA Adapter Index. RECORD Index number/SAMPLE 2. Mix well by pipetting.

3. Incubate:
   a. 30° C.-10 min
4. Add 1.67 µL of Stop Ligase Mix to inactivate ligation. Mix well by pipetting.

AMPure® Clean Up after Ligation=DOUBLE PURIFICATION
1. [1st Purification] Vortex the AMPure® XP beads until they are homogenous. Add 14 µL of the AMPure® XP beads to the sample tube (~100 µL) and mix by pipetting.
2. Incubate at RT for 15 min.
3. Place the tube at magnetic stand for 5 min
4. Discard supernatant.
5. Wash the beads with 200 µL of 80% EtOH without disturbing the beads.
6. Wait 30 sec. Discard the supernatant.
7. Repeat the wash with 80% EtOH
8. Air dry the beads for 15 min at RT
9. Resuspend the beads in 52 µL of Resuspension Buffer. Mix by pipetting.
10. Incubate the sample at RT for 2 min
11. Place sample in Magnetic stand for 5 min.
12. Transfer the supernatant (ds cDNA, 50 µL) to a new tube.
13. [2nd Purification] Vortex the AMPure® XP beads until they are homogenous. Add 5 µL of the AMPure® XP beads to the sample tube (~100 µL) and mix by pipetting.
14. Incubate at RT for 15 min.
15. Place the tube at magnetic stand for 5 min
16. Discard supernatant.
17. Wash the beads with 200 µL of 80% EtOH without disturbing the beads.
18. Wait 30 sec. Discard the supernatant.
19. Repeat the wash with 80% EtOH
20. Air dry the beads for 15 min at RT
21. Resuspend the beads in 9.67 µL of Resuspension Buffer. Mix by pipetting.
22. Incubate the sample at RT for 2 min
23. Place sample in Magnetic stand for 5 min.
24. Transfer the supernatant (ds cDNA, 7.67 µL) to a new tube.

PCR
1. Add the following:°
   a. 1.67 µL PCR Primer Cocktail
   b. 8.33 µL PCR Master Mix
2. Mix well by pipetting
3. Incubate:
   a. 98° C.-30 sec
   b. 15 cycles of:
      i. 98° C.-10 sec
      ii. 60° C.-30 sec
      iii. 72° C.-30 sec
   c. 72° C.-5 min
   d. 4° C.-hold The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A method for preparing circular double stranded DNA substantially free of linear genomic DNA (gDNA) comprising the steps of:
   a) forming a cellular lysate by lysing mammalian cells containing linear genomic DNA of length greater than a billion base pairs and circular double stranded DNA of length less than 30,000 base pairs;
   b) incubating said lysate with an amount of Proteinase K effective to digest proteins in said lysate;
   c) digesting any RNA in said lysate;
   d) adding a Protein Precipitation reagent to said lysate to obtain a precipitate and a supernatant;
   e) precipitating total DNA in said supernatant and forming a pellet;
   f) suspending the supernatant pellet in a buffer;
   g) incubating the suspended pellet at about 70° C. for about 30 minutes to form a solution;
   h) incubating the solution containing the pellet with an amount of an Exonuclease, selected from the group consisting of Hind Exonuclease V, T5 exonuclease, and Exonuclease V for a time and at a concentration effective to cleave linear genomic DNA and obtain circular double stranded DNA;
   i) incubating said circular double stranded DNA with an amount of carboxylated solid phase reversible immobilization magnetic beads effective to bind to said circular double stranded DNA; and
   j) washing said beads with ethanol and eluting said circular double stranded DNA from said pellet,
   wherein the method is free of ultra-centrifugation and provides circular double stranded DNA from mammalian cells that is at least 90% free of linear genomic DNA.

2. A method for preparing circular double stranded mitochondrial DNA (mtDNA) substantially free of linear genomic DNA (gDNA) comprising the steps of:
   a) providing a solution comprising circular, double stranded mitochondrial DNA (mtDNA) and linear genomic DNA (gDNA) purified from a mammalian cell having linear genomic DNA of length greater than a billion base pairs and circular double stranded mtDNA of length less than about 30,000 base pairs;
   b) incubating the solution with an amount of an Exonuclease selected from the group consisting of Hind Exonuclease V, T5 exonuclease, and Exonuclease V for a time and at a concentration effective to cleave linear genomic DNA and obtain circular, double stranded mtDNA;
   c) incubating said circular double stranded mtDNA with an amount of carboxylated solid phase reversible immobilization magnetic beads effective to bind said circular double stranded mtDNA;
   d) washing said beads with ethanol;
   e) eluting said circular double stranded mtDNA from said beads,
   wherein said method is free of ultra-centrifugation and provides circular double stranded mtDNA from mammalian cells that is at least 90% free of linear genomic DNA; and
   f) evaluating the purity of the circular double stranded mtDNA by amplifying the genomic and mt DNA using genomic and mitochondrial specific primers.

3. A method for preparing circular double stranded mitochondrial DNA substantially free of linear genomic DNA (gDNA) comprising the steps of:

a) providing a cellular lysate by lysing mammalian cells having about 6 billion base pairs of linear genomic DNA and about 16,000 base pairs of circular double stranded mt DNA and free of protein and RNA contaminants;
b) precipitating cellular debris and proteins out of said lysate and obtaining a solution comprising purified circular double stranded mitochondrial DNA (mtDNA) and linear genomic DNA (gDNA);
c) incubating said solution with an amount of an Exonuclease, selected from the group consisting of Hind Exonuclease V, T5 exonuclease, and Exonuclease V for a time and at a temperature effective to cleave linear genomic DNA and obtain circular double stranded mtDNA;
d) incubating said circular double stranded mtDNA with an amount of carboxylated solid phase reversible immobilization magnetic beads effective to bind said circular double stranded mtDNA;
e) washing said beads with ethanol,
f) eluting said mtDNA from said beads, and
g) evaluating the purity of the mtDNA by amplifying the linear genomic and circular double stranded mt DNA using genomic and mitochondrial specific primers,
wherein said method is free of ultra-centrifugation and provides mtDNA from the mammalian cells that is at least 90% free of linear gDNA.

4. A method for preparing circular double stranded DNA substantially free of linear DNA comprising the steps of:
a) providing a lysate from mammalian cells having about 6 billion base pairs of linear DNA and about 16,000 base pairs of circular, double-stranded DNA that is free of protein and RNA contaminants;
b) incubating said lysate with an amount of an Exonuclease, selected from the group consisting of Hind Exonuclease V, T5 exonuclease, and Exonuclease V for a time and at temperature effective to cleave linear DNA and obtain circular double stranded DNA;
c) incubating said circular double stranded DNA with an amount of carboxylated solid phase reversible immobilization magnetic beads effective to bind said circular double stranded DNA;
d) washing said beads with ethanol, and
e) eluting said circular double stranded DNA from said beads,
wherein said method is free of ultra-centrifugation and provides circular double stranded DNA from mammalian cells that is at least 80% free of linear DNA.

5. The method of claim 4 wherein said circular double stranded DNA is mtDNA.

6. The method of claim 1 wherein the circular double stranded DNA is a mtDNA that is at least 95% free of linear gDNA.

7. The method of claim 2 wherein said method provides mtDNA that is at least 95% free of linear gDNA.

8. The method of claim 3 wherein said method provides mtDNA that is at least 95% free of linear gDNA.

9. The method of claim 4 wherein the circular double stranded DNA is a mtDNA that is at least 95% free of linear gDNA.

\* \* \* \* \*